(12) United States Patent
Stoddart et al.

(10) Patent No.: US 6,381,480 B1
(45) Date of Patent: Apr. 30, 2002

(54) METHOD AND APPARATUS FOR MONITORING FETAL CEREBRAL OXYGENATION DURING CHILDBIRTH

(76) Inventors: Hugh Franklin Stoddart, P.O. Box 200, Groton, MA (US) 01450; Hugh Adam Stoddart, 8 Mill Rd., Harvard, MA (US) 01451; Thomas C. Sefranek, 112 Great Rd., Shirley, MA (US) 01464

( * ) Notice: Subject to any disclaimer, the term of this patent is extended or adjusted under 35 U.S.C. 154(b) by 0 days.

(21) Appl. No.: 09/555,351
(22) PCT Filed: Nov. 25, 1998
(86) PCT No.: PCT/US98/25236
    § 371 Date: May 26, 2000
    § 102(e) Date: May 26, 2000
(87) PCT Pub. No.: WO99/26528
    PCT Pub. Date: Jun. 3, 1999

Related U.S. Application Data
(60) Provisional application No. 60/066,596, filed on Nov. 26, 1997.

(51) Int. Cl.[7] .................................. A61B 5/00
(52) U.S. Cl. ....................................... 600/338
(58) Field of Search ................... 600/300, 310, 600/313, 323, 326, 327, 338, 341, 342, 473; 356/39, 300, 317, 337; 422/82.05, 82.09; 436/63, 164, 171

(56) References Cited

U.S. PATENT DOCUMENTS

| 5,309,907 | A |   | 5/1994 | Fang et al. |
| 5,524,617 | A | * | 6/1996 | Mannheimer ............... 600/323 |
| 5,551,424 | A |   | 9/1996 | Morrison et al. |
| 5,770,454 | A |   | 6/1998 | Essenpreis et al. |
| 5,782,237 | A | * | 7/1998 | Casciani et al. ............ 600/323 |

* cited by examiner

Primary Examiner—Eric F. Winakur
(74) Attorney, Agent, or Firm—Price, Heneveld, Cooper, DeWitt & Litton

(57) ABSTRACT

An apparatus is disclosed for monitoring fetal cerebral oxygenation during childbirth. The apparatus includes a tunable source of infrared photons, a probe to access a single location on the scalp of the fetus for injecting the infrared photons generated by the photon source, and for receiving scattered photons reflected from within the skull of the fetus. The apparatus at least has first and second detectors for detecting the presence of photons received through the probe at selected different delay intervals so as to be capable of distinguishing photons reflected from different depths or at different instances from within the head of the fetus.

30 Claims, 9 Drawing Sheets

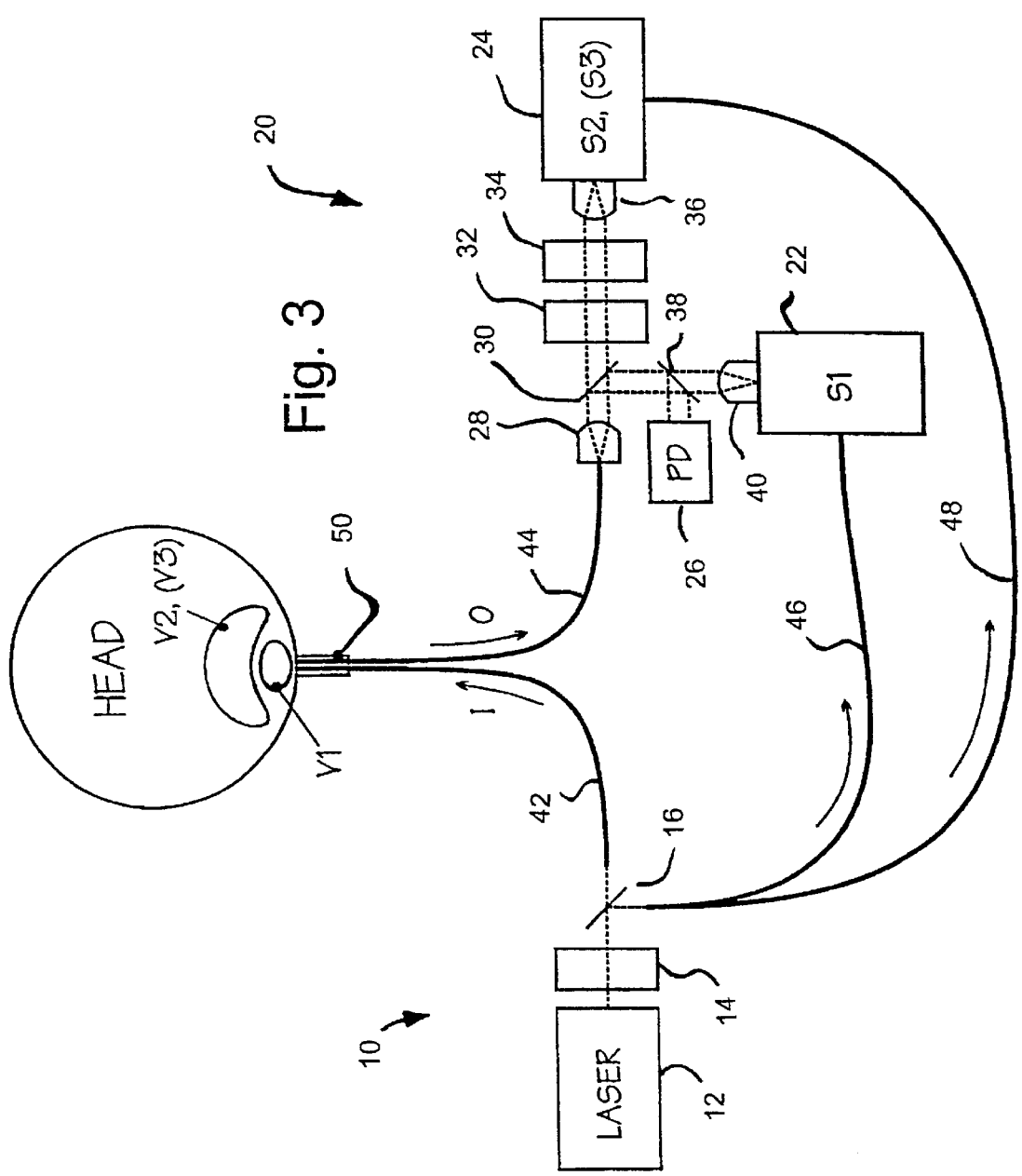

METHOD AND APPARATUS FOR MONITORING FETAL CEREBRAL OXYGENATION DURING CHILDBIRTH

This Application is 937/ of PCT/US98/25236 filed Nov. 25, 1998 which claims benefit of Provisional No. 60/066,596 filed Nov. 26, 1997.

BACKGROUND OF THE INVENTION

The present invention generally pertains to a method and apparatus for monitoring fetal cerebral oxygenation during childbirth. More particularly, the present invention relates to a method and apparatus for monitoring fetal cerebral oxygenation using near-infrared spectroscopy.

As is well known, oxygen is transferred from the maternal blood to the fetal circulation through the placenta. During uterine contractions, increased pressure on the placenta impedes blood flow and interrupts the supply of oxygen to the fetus to a degree proportional to the duration, intensity, and frequency of the contractions. The fetus has a number of protective mechanisms including a special form of hemoglobin, with its dissociation curve shifted to the left, which binds more oxygen at lower partial pressures. Also, when the oxygen supply is cut off, the fetal metabolism continues to produce chemical energy (ATP) by anaerobically converting glucose to lactate—"glycolysis." (Red cells themselves do not use oxygen but get all their energy this way.) Reestablishment of blood flow provides the oxygen to metabolize the excess lactate and return cells to normal metabolism.

Despite these protective measures, if the fetus is compromised by a sustained interruption of the blood supply or when the normal placental vasculature is impaired, profound fetal hypoxia can result in permanent brain damage or death. If fetal hypoxia is detected early enough, an operative delivery can be initiated to prevent or reduce brain damage. There are presently no good ways to monitor fetal oxygenation distress.

The fetal heart rate slows in response to low oxygenation (opposite to adults) and may be monitored either externally using Doppler ultrasound and other methods, or directly by hooking a small electrode into the fetal scalp. The latter is more reliable and is becoming more commonly used. Late slowing of the heart rate (decelerations) during each uterine contraction are thought to result from uteroplacental insufficiency and reflect inadequate fetal oxygenation. While very sensitive, the technique has such low specificity that it may lead to unjustified operative deliveries.

Because fetal cerebral oxygenation is not now directly measurable, consideration has been given to measuring the fetal scalp oxygenation in the hope it will provide some information—even though its relationship to what is going on in central and cerebral oxygenation remains highly controversial. However, even though some of the fetal scalp is accessible early, the direct measurement of scalp oxygenation has many practical problems.

Blood samples are occasionally taken from the scalp for analysis, but this has the disadvantage of limited availability, prerequisites for use, and invasive nature. Moreover, however accurate, sampling provides only intermittent information about the very dynamically changing condition of the fetus during labor.

Continuous monitoring of blood pH (an indication of oxygenation) in the subcutaneous space of the fetal scalp through a hollow spiral needle has been described but is expensive and not used outside of clinical research centers.

Transcutaneous oxygen tension ($tcPO_2$) using a Clark-type electrode is possible but requires a tight, dry seal between the scalp and the surface of the electrode. Other disadvantages include the need to constantly heat the skin under the electrode in order to increase oxygen diffusion through the skin, the slow response time of the electrodes, the dependence on the measurement on skin blood flow, and the inherent long-term drift of the $tcPO_2$ electrodes.

Recently, in vivo near-infrared spectroscopy (NIRS) has shown considerable promise for noninvasive, direct monitoring of fetal and neonatal cerebral tissue oxygenation. The basis of the methodology is the surprising translucence of the body to near-infrared photons having wavelengths between about 700 and 1100 nm. The light is easily seen transmitted through thin body parts (cheek, ear, fingers, etc.) and a "back-scattered" halo of reflected light can be observed from all, including thick tissues, and invisible near-infrared light is far more easily transmitted. The very long (random and tortuous) paths taken by the photons makes them exceedingly sensitive to the optical properties of tissue and, in particular, the concentration of hemoglobin molecules and the average amount of oxygen they are carrying.

Measuring available oxygen is very useful. At any moment, the body's total supply of oxygen is only about one gram (just enough to last about four minutes), which is bound to the hemoglobin in circulating blood. Obviously, maintenance of the oxygen supply is crucial to avoid irreversible tissue death. The length of time that cells can survive following interruption of oxygen depends on the type of tissue. Brain neurons are unrecoverable after only several minutes.

Measurement of just how much oxygen hemoglobin is carrying is made possible because the infrared (and visible "color") absorption spectrum of hemoglobin is strongly dependent on its oxygen saturation. Arterial blood leaving the heart gets its bright red color from hemoglobin that is nearly saturated with oxygen absorbed in the lungs. The hemoglobin of venous blood has given up much of its oxygen to tissue metabolism and turned dark and bluish.

The average amount of oxygen carried by hemoglobin molecules is expressed as the percent of "saturation." Thus, hemoglobin in arterial blood, having just visited the lungs, is nearly 100% saturated. Many of the hemoglobin molecules in the venous blood will have given up this oxygen to the cells of the body and the average saturation may fall to half (50%) or less.

The nomenclature is mixed, but a hemoglobin molecule that has oxygen attached to all four binding sites is called "oxy-hemoglobin." Hemoglobin without any oxygen attached is called "deoxy-hemoglobin." Individual hemoglobin molecules will be in one state or the other, since it is very unlikely that any hemoglobin molecule will have only partial filling of its four oxygen-binding sites.

NIRS technology uses a source of near-infrared light to send photons into the skin over the organ of interest. After being scattered about inside the body, some photons survive to return and exit the skin. A detector at some nearby point measures their flux compared to the injected flux ("reflectance"). Reflectance is defined as the number of returning photons per unit area per photon injected and is essentially an exponentially decreasing function of the effective absorption coefficient $\mu_{eff}=\sqrt{(3\mu_a\mu_s')}$ and the distance between source and detector.

Both the light source (typically a light emitting diode or tungsten lamp) and the detector (typically a silicon photodiode or photomultiplier) are called "optodes." By doing this measurement at several wavelengths, one can infer the spectral absorptance, and hence estimate the concentration of hemoglobin (and hence blood) in the organ and its average oxygenation.

The "pulse oximeter" was the first successful device based on measuring infrared spectral reflectance, and is very widely used. It is an extension of the infrared heart rate monitors that can be clipped to the earlobe or finger and detect the change of light absorption as arteries in the light path expand and contract in response to pressure from heart muscle contractions. By detecting the change of absorption at two or more wavelengths, pulse oximeters can measure the average hemoglobin oxygen saturation in the pulsing arteries. By their nature, pulse oximeters are insensitive to the oxygenation of capillary and venous blood—or, for that matter, arterial blood that is remote from the skin surface. Since the small changes in absorption are easily swamped by changes in optode spacing, pulse oximeters are very sensitive to patient motion.

Although manufacturers are attempting to adapt pulse oximeters to measure oxygenation of the fetal brain during birth, they are not well suited for this special application. Even if they can be made to reliably measure arterial oxygen saturation in the fetal scalp in the presence of massive subject motion, the blood flow may be so low that the brain is oxygen-starved while the arteries in the scalp are 95% oxygen saturated.

A more recent application of NIRS technology is typified by the Cerebral Oximeter (INVOS 3100) made by Somanetics Corporation of Troy, Mich., which currently is the only FDA-approved NIRS medical device that is sensitive to deep arterial and venous blood oxygenation. The theory behind the Somanetics instrument is as follows. Near-infrared light photons are injected into the skin over the forehead. After being scattered about inside the skin, scalp, skull, and brain, some fraction of the photons survive to return and exit the skin several centimeters away. By measuring the flux of returning photons as a function of wavelength, one can infer the spectral absorptance of the blood in the underlying tissue. For further information, reference is made to Somanetics U.S. Pat. Nos. 4,570,638, 4,725,147, 4,768,516, 4,817,623, 5,139,025, 5,140,989, 5,217,013, 5,349,961, 5,465,714, 5,477,853, 5,482,034, 5,584,296, and 5,697,367. FIG. 1 is a plot of the hemoglobin absorption coefficient as a function of wavelength for hemoglobin having 100% oxygen saturation and hemoglobin having no oxygen.

In order to insure that the photons penetrate deep enough to sample brain tissue, it is necessary to provide a substantial separation between the source and detector optodes. Intuitively, the greater the separation of optodes, the greater the average depth of penetration. Photons that happen to meander close to the surface are very likely to be lost out of the skin before reaching the distant detector. Large optode spacings are therefore biased against "shallow" photons, except in the immediate vicinity of the source and detector. On the other hand, increasing path lengths and absorption also make it unlikely that very deeply penetrating photons will find their way back to the detector. Most of the photons reaching the detector will have taken some optimum middle course. It turns out that the average penetration is about 30% of the source/detector spacing.

The unique feature of the Somanetics sensor is that it has two different optode spacings. Data from the smaller, 3 cm spacing (shallower penetration) is subtracted from the larger, 4 cm spacing, which enables suppression of some of the sensitivity to scalp and skull hemoglobin oxygenation while emphasizing the brain oxygenation.

The main drawback to the direct use of NIRS is the requirement for at least two separated optodes (and perhaps a third if scalp oxygenation is to be suppressed) optically connected to the fetal scalp and separated by sufficient distance to insure reflected light has reached the brain. The very considerable practical difficulties of doing this in the hectic birthing environment has discouraged fetal use despite success with the adult head.

SUMMARY OF THE INVENTION

Accordingly, it is an aspect of the present invention to solve the above problems by providing an apparatus for monitoring fetal cerebral oxygenation during childbirth using a noninvasive probe that may be positioned on the scalp of a fetus at a single location. To achieve this and other aspects and advantages, the apparatus constructed in accordance with the present invention comprises a source of infrared photons, a probe to be disposed on a single location on the scalp of a fetus for injecting the infrared photons generated by the photon source and for receiving scattered photons reflected from within the skull of the fetus, and first and second detectors for detecting the presence of photons received through the probe at two different delay intervals so as to be capable of distinguishing photons reflected from different depths within the head of the fetus.

These and other features, advantages, and objects of the present invention will be further understood and appreciated by those skilled in the art by reference to the following specification, claims, and appended drawings.

BRIEF DESCRIPTION OF THE DRAWINGS

In the drawings:

FIG. 3 is a schematic diagram of an apparatus constructed in accordance with the present invention;

FIG. 4 is a schematic diagram of an image intensifier used in the present invention;

DETAILED DESCRIPTION OF THE PREFERRED EMBODIMENTS

The method of the present invention includes the steps of injecting a pulse of photons into the head, waiting for them to sample the cerebral tissue by scattering about, and then detecting surviving photons exiting the head at the injection site. Because photons are temporarily "stored" inside the head, the method is referred to as "infrared photon storage" or simply "IRPS." IRPS is a novel alternative to achieving depth sensitivity in which temporal separation replaces the need for spatial separation of optodes.

This noninvasive approach has the potential for providing crucial information on changes in fetal cerebral oxygenation without materially adding to the complexity of instrumentation currently used during birthing or increasing the duties of the attendants.

Figure 1:
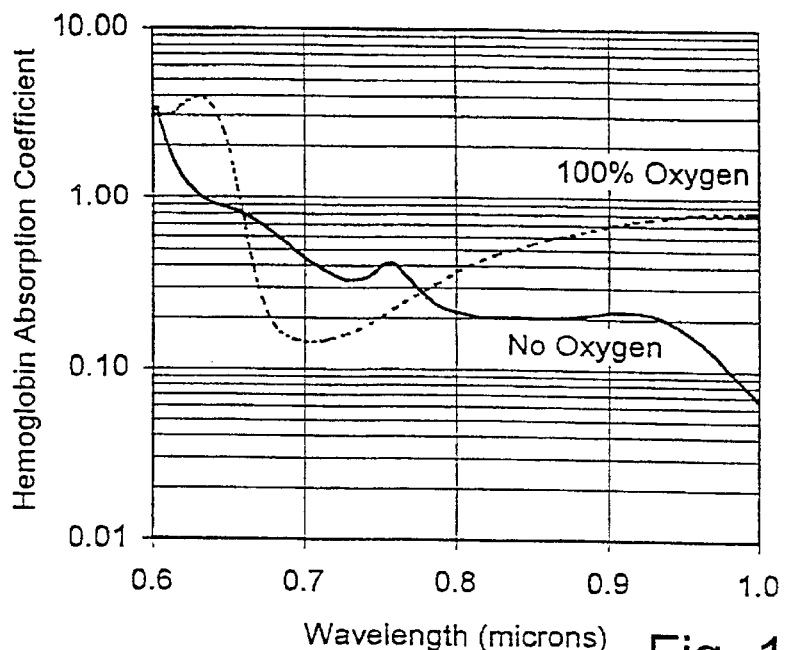
FIG. 1 is a graph showing the hemoglobin absorption coefficient versus wavelength for hemoglobin that is saturated with oxygen and hemoglobin that carries no oxygen.
Figure 2:
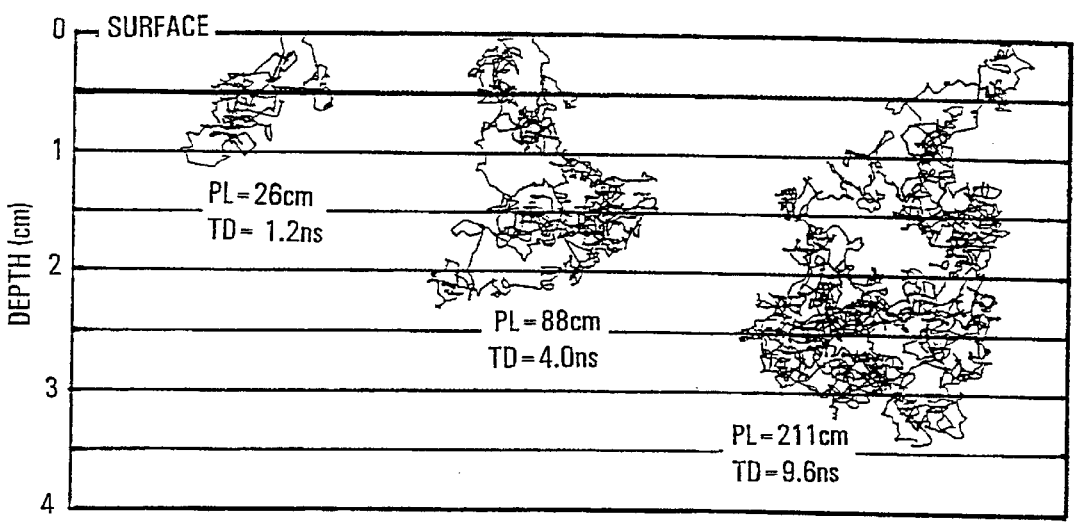
FIG. 2 is a diagram illustrating sample photon paths as a function of reemergence delay.

An injected pulse of photons will spread by diffusion away from the probe, either penetrating into the head or reflecting back and escaping into the air. As time goes on, the density of left-over shallow photons becomes low compared to captured deep photons because it is unlikely that a photon in the scalp will remain there for a long time (it will either exit through the skin or penetrate deeper). The longer one waits to sample returning photons, the deeper, on average, they will have penetrated. Examples of photon paths which enter and leave the head at the same site are shown in FIG. 2.

Clearly, the longer one waits to detect the exiting photon, the deeper it will have penetrated into the head and its sensitivity to the optical parameters of deeper tissue (brain) will be greater than that for shallow tissues (scalp and skull) because its path is relatively longer.

As shown in FIG. 3, the apparatus constructed in accordance with the present invention generally includes a source of photons 10, a photon detection device 20, and an applicator 50 for operatively connecting the photon source 10 and detecting device 20 to the scalp of a fetus. Photon source 10 preferably includes a laser 12 having the capability of generating very short pulses of injected light at a plurality of useful wavelengths in the infrared that are injected into the head of the fetus.

Laser 12 (for example, a nitrogen-pumped dye laser or a Q-switched "YAG" laser) produces a short (e.g., $\leq 5$ ns) intense ($10^{15}$ or more photons) pulse of infrared light, which is conducted by means of a fiberoptic cable "I" 42 to the baby's head. Photons leaving the head are conducted by a fiberoptical cable "O" 44 to a set of detectors and shutters forming detection device 20. Detection device 20 includes a lens 28 that expands and collimates the returning photons. A small fraction of the returning photons (about 10%) are sent to a silicon photodiode detector "PD" 26 and a first shuttered detector "S1" 22 using partially reflecting mirrors 30 and 38. Most of the light proceeds to a second shuttered detector "S2" 24. Lenses 36 and 40 are used to focus the collimated beam onto shuttered detectors 22 and 24.

Photon source 10 and detector device 20 each include an auxiliary shutter 14 and 32. Detector device 20 also includes a fluorescence-blocking filter 34. The roles of filter 34 and auxiliary shutters 14 and 32 are discussed below. Also discussed below is the method for attaching the fiberoptic cables 42 and 44 to the head.

The apparatus of the present invention may also include a saturable absorption filter (not shown) positioned between the laser (or other photon source) and fiberoptic cable 42. Such saturable absorber filters typically include an absorbing dye dissolved in a plastic. These dyes generally absorb at the laser wavelength, unless the laser light becomes so strong that it occupies all of the available energy levels for a given concentration of dye at which point the saturable absorption filter becomes transparent. By utilizing such a filter, only that portion of a photon pulse generated by the laser that has a certain intensity will be injected into the fetus, and any echoing in fluorescence in fiber 42 would be stopped.

Shuttered detectors 22 and 24 are designed to be turned on (opened) by a pulse of light and to stay on (open) for a time equal to the duration of the applied pulse. A small fraction of the output of the laser (<10%) is conducted to shuttered detectors 22 and 24 by means of fiberoptic cables 46 and 48 and a partially reflective mirror 16.

The length of cable 46 is adjusted so that first shuttered detector 22 is opened a short time (~1 ns) after the photons are injected into the head. However, the length of cable 48 is adjusted so that second shuttered detector 24 is opened considerably later—typically, several nanoseconds after the photons are injected. The result is that photodetector 26 integrates all emerging photons including those that get into cable 44 during the laser pulse. First shuttered detector 22 sees photons that have been stored mainly in the scalp and skull "V1," while second shuttered detector 24 sees photons that have been stored mainly in the brain "V2." There are some potential advantages to having a third shuttered detector "S3" which, like second shuttered detector 22, has a long (but different) gate delay that also samples a deep volume (V3). Having two long-delay (but different) shuttered detectors (S2, S3) and two alternating wavelengths, permits the oxygenation to be determined while suppressing subject-dependent parameters and variations in skin contact. Adding information from the short delay shuttered detector (S1) helps to further suppress sensitivity to the scalp and skull, while the prompt data from the silicon photodiode (PD) gives information about the optical contacts.

Laser diodes may be commercially preferable for providing the injection light pulse. Their small cavities make possible pulse widths of 50 ps at repetition rates up to 10 MHz. However, a nitrogen-pumped dye laser offers very much more pulse power, any wavelength, quick delivery, and a history of reliability. A Model LN1000 Nitrogen Laser and Model LN102 Dye Laser from Laser Photonics of Orlando, Fla., were used to construct an exemplary prototype. The nitrogen laser has an energy output of 1.4 mJ per 600 ps second pulse giving rise to a peak power of 2.3 megawatts. Excited by the nitrogen laser, the tunable dye laser has an output of 250 $\mu$J and a 500 ps pulse width. The system is capable of up to 20 pulses per second.

Various dyes were used spanning wavelengths from 500 to 830 nm. Coumarin 500 was dissolved in ethanol (100 mg in 50 ml) to generate light at 510 nm. Wavelengths near 605 were produced with rhodamine B in ethanol at the same concentration. Several infrared fluorescing dyes were tried ending with styryl 9M in DMSO, again at the same concentrations, which peaked at 829 nm. By using a tunable laser, the wavelength of each successive pulse of injected photons may be varied as is common place in cerebral oximeters.

The shutter for each shuttered detector 22 and 24 must be very fast acting - going from completely "off" to "on" in about a nanosecond or less. The ratio off to on sensitivity is often called the "shutter ratio" or switching ratio. A second important requirement is reproducibility of the turn-on-time - usually called "jitter." For the reasons described below, errors of nanoseconds in turn-on relative to the injected pulse time are intolerable. Finally, besides these technical requirements, the shutter should be rugged, reliable, and relatively inexpensive.

Spinning devices and nano-sized piezo configurations for mechanical shutters may also meet these requirements, but are presently considered overly complicated. Optical shutters based on the Kerr or Pockels effects may also be useful but, while fast enough, tend to have poor shutter ratios (limited to about two decades).

The first embodiment uses the combination of a shutter and detector by gating a fast, linear, focused-dynode PMT. In the "off" condition, the photocathode would be biased positive relative to the first dynode. A negative pulse applied to the photocathode would be used to gate it "on." Specifically, the first embodiment was constructed using an image intensifier of the type widely used by the military in night vision devices. They are mass-produced, relatively inexpensive, necessarily very rugged, and, by design, very light sensitive.

A schematic cross section of a modern, proximity-focused image intensifier is shown in FIG. 4. It consists of an entrance window "A" with a very sensitive (to near-infrared light) photocathode 60 deposited on its inner surface. A few hundred microns from the photocathode is in the input face of the microchannel plate electron multiplier (MCP) "B." The electrons emerging from the MCP are accelerated to a phosphor screen 62 deposited on the inside of the output window "C." Thus, a few photons arriving at photocathode 60 can (depending on the quantum efficiency of the photocathode material) produce a photoelectron which is collected and multiplied by the MCP, with typical gains over $10^3$.

These electrons are accelerated to several keV before striking the output phosphor 62. Each electron produces about 20 visible photons for each keV of energy deposited. The overall photon gain (photons out per photons in) can easily exceed $10^4$.

Image intensifiers have been used as fast electronic imaging shutters, with the photocathode 60 held "off" by reverse "biasing" it electrically positive relative to the front of the MCP. To momentarily turn the image intensifier "on" (open the shutter), a short negative pulse is applied to photocathode 60 with sufficient amplitude to overcome the "off" bias and allow the photoelectrons to proceed to the MCP. The speed with which an image intensifier can be turned on and off is limited by a phenomenon called "irising" in which the peripheral image field appears first while the center of the field is still dark (off). The reason is that the photocathode material has a relatively high resistance per unit area and a distributed capacitance, principally to the front of the MCP. When a negative pulse is applied to an electrode ring 64 contacting photocathode 60, it takes time to charge the photocathode center relative to the periphery. It typically takes at least several nanoseconds to get an image intensifier fully turned on.

However, irising is irrelevant for this application, since the image intensifier is only used for shuttered photon detection rather than shuttered electronic imagery. By limiting the receiving fiberoptics to the edge of the photocathode adjacent to its ring electrode 64, the problem is avoided altogether.

The fact that the image intensifier output is light rather than electrical energy (as would be the case with a gated PMT) is also useful because it provides optical isolation from the fast, negative-pulse transient that gates photocathode 60 on.

The negative photocathode gating pulse to the image intensifier must have rise times of less than a nanosecond, amplitudes of tens of volts, and must not "jitter" more than fractional nanoseconds from the timing of the injected light pulse. None of these requirements are easily attained. One way to meet the jitter requirement is to initiate the gating pulse directly from the laser light pulse. There is, however, some jitter in the UV laser between the time of the electrical pulse-initiating discharge and the appearance of the light pulse. One way to avoid such jitter is to use a PMT to produce a large, fast, negative gating pulse directly from a fraction of the light pulse taken from either the dye or UV laser. The current required to charge the capacitance of the anode of the PMT, the photocathode of the image intensifier, and the wiring in a nanosecond is substantial. Assuming a 20v pulse is needed and the total load capacitance is $50 \times 10^{-12}$ farads, the charge required is:

$$Q = CV = 50 \times 10^{-12} \times 20 = 1 \times 10^{-9} \text{ coulombs}$$

In order to charge the load capacitance in 1ns, at least an ampere of current is needed from the photomultiplier:

$$I = C \times \frac{dv}{dt} = 50 \times 10^{-12} \times \frac{20}{1 \times 10^{-9}} = 1 \text{ ampere}$$

To determine how much current could be supplied from the photocathode by itself, all the other electrodes were tied together. With -100v on the photocathode of an RCA 4523, it was exposed to the <1 ns light (510 nm) pulse from the dye laser. This configuration produced a 6v negative pulse on the other electrodes as measured with a 1 MΩ scope probe. Assuming a minimum stray capacitance of 20 pF, this corresponds to a charge of about $10^{-10}$ coulombs (equivalent to about $6 \times 10^9$ photoelectrons). The signal was not substantially reduced when a business card was placed between the laser beam and the photocathode, indicating that the small-diameter laser beam was locally saturating the photocathode. When the light was diffused over the entire photocathode by the business card, it became much less saturated, compensating for the very considerable loss of intensity.

The charge released from the photocathode alone corresponds to a current of 0.1 ampere in less than a nanosecond that the laser is on. This meant that very few dynodes would be needed to get to currents of several amperes.

Figure 5:
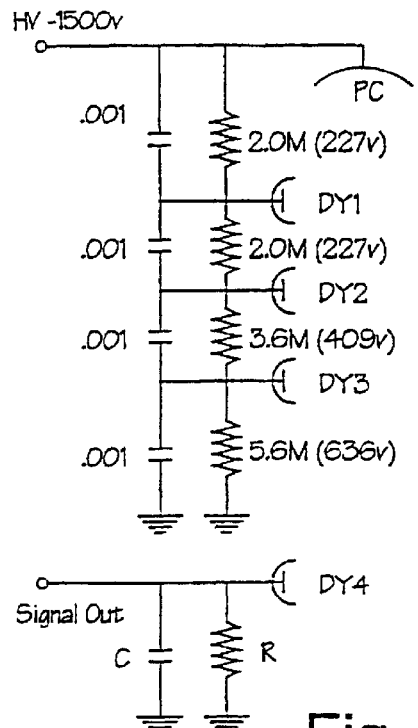
FIG. 5 is an electrical circuit shown in schematic form illustrating a photomultiplier tube (PMT) circuit used to gate an image intensifier of the present invention.

The photocathode may be configured using the first three dynodes for gain and the fourth as an anode, or the first four dynodes for gain and the fifth connected as the anode. All the other dynodes may be connected together to ground or to a small negative bias. A generic schematic of such a configuration is shown in FIG. 5. Dynode voltages are made large to reduce transit time and transit time spread. Additional voltage is applied to the last dynodes to overcome large space charges at these very high currents. The "signal out" pulse of electrons goes directly to the intensifier photocathode to turn it on. Resistor "R" can be set to match the impedance of a connecting cable and may be returned to a positive voltage to bias the intensifier photocathode off between pulses. A positive pulse may be taken from third dynode (DY3) as a convenient way of triggering the scope used to measure the various signals. Capacitor "C" is normally not added to the circuit, but is a convenient way to measure the charge produced in a pulse. Typical output currents ranged from 2 to 20 amperes.

Figure 6:
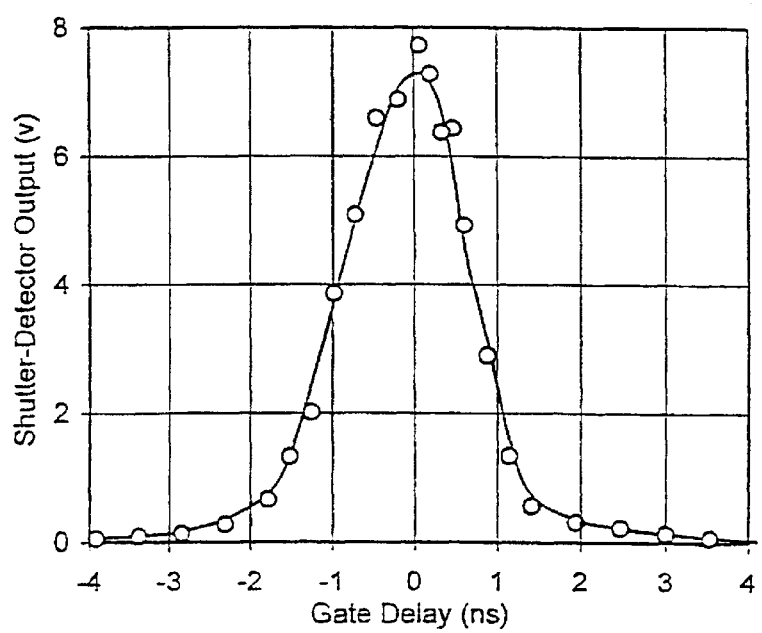
FIG. 6 is a graph showing a cross correlation curve recorded using a second embodiment of the present invention.

A second embodiment was constructed using a 2060 PMT in place of the 4523. Using the second embodiment, a first cross correlation curve was recorded (shown in FIG. 6) between the temporal distribution of the laser pulse and the temporal distribution of the shutter detector sensitivity using the experimental setup described in the next section. Assuming an initially rapid rising, then more gradually saturating laser pulse that suddenly terminates followed by a small tail, and, assuming a shutter that turns on and off very quickly (also with a small tail), the slightly asymmetrical shape is about what one would expect.

Figure 7:
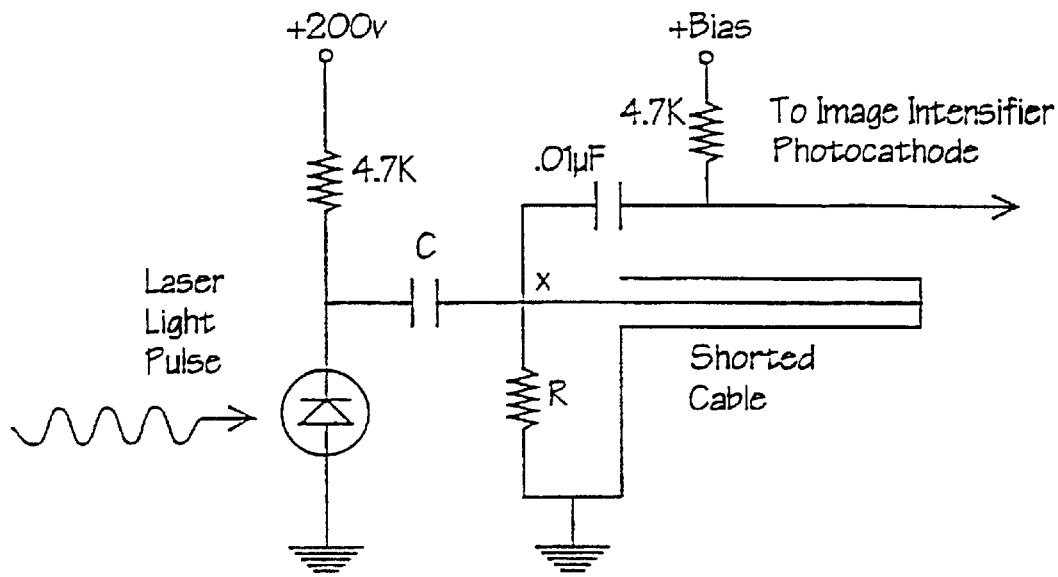
FIG. 7 is an electrical circuit diagram in schematic form showing a photodiode circuit used to gate an image intensifier constructed in accordance with a third embodiment of the present invention.

A third embodiment was constructed having a circuit like that shown schematically in FIG. 7 to replace the PMT gate trigger in the second embodiment. Between laser pulses, capacitor "C" is charged to about 200v (the "back-voltage" on the silicon photodiode). When the diode is turned on by the laser light pulse, point "x" goes rapidly negative. A quick recovery is provided by the pulse-shaping cable (CD50034), which returns an inverted pulse from its shorted end. Resistor "R" is used to match the cable impedance. At the expense of some "ringing," it may be removed to increase the gate signal. The negative-going gate signal is capacitively coupled to the image intensifier photocathode, which is biased positive, and hence off, relative to the MCP input.

Figure 8:
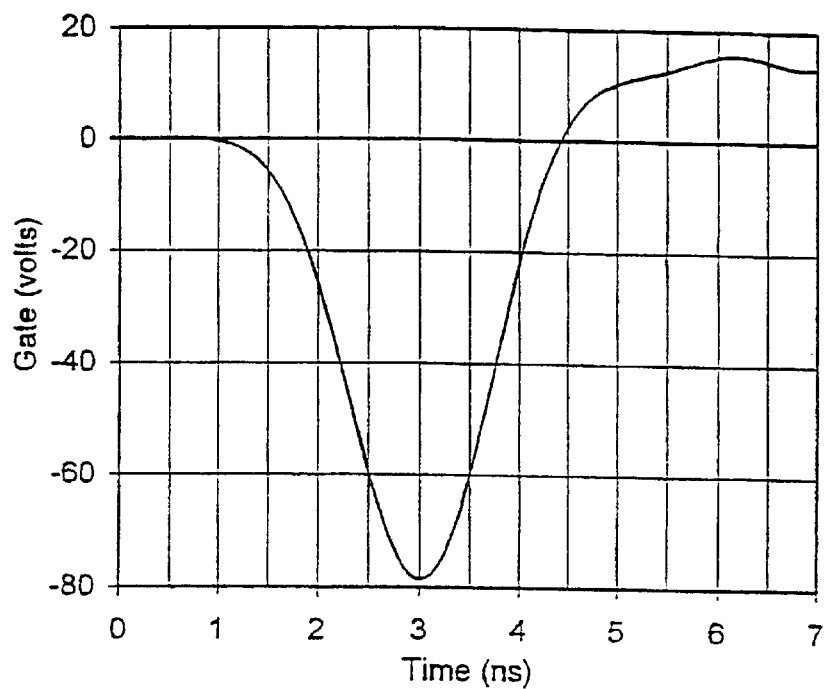
FIG. 8 is a graph illustrating an oscilloscope trace of a photodiode-generated gate pulse used in the third embodiment of the present invention.

In the third embodiment, three photodiodes were used in parallel to increase the gate signal. A trace of the gate wave-form is shown in FIG. 8. It is probably faster than this since the measurement was taken with a 10 pF scope probe connected at point "x" in FIG. 7. The Tektronics (Model TDS 380) scope bandwidth is limited to 400 MHz. Note that the photocathode is normally biased off by −60v, and only the portion between −60 and −80v is used to provide the gate.

Figure 9:
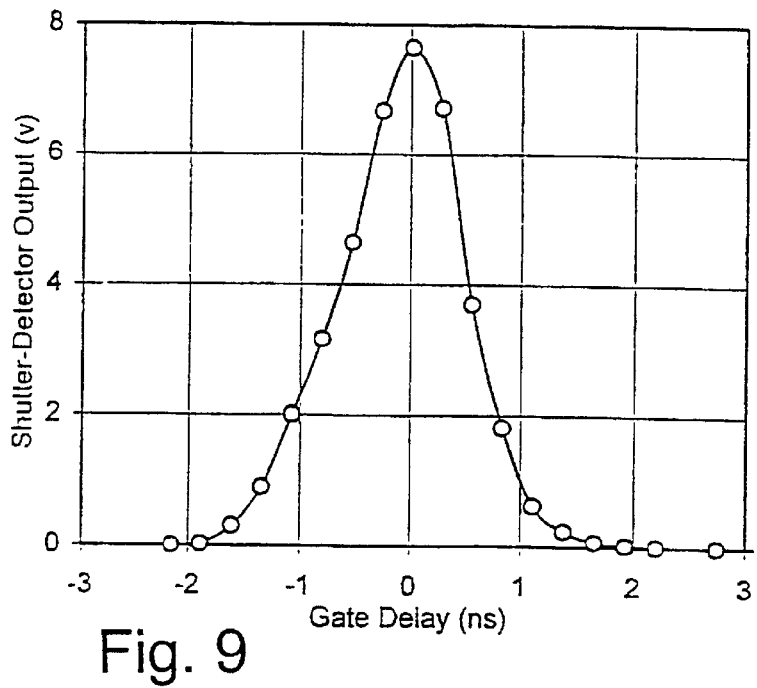
FIG. 9 is a graph showing a cross correlation curve recorded using the third embodiment of the present invention.

A cross correlation curve recorded using the third embodiment (to be compared to the curve shown in FIG. 6) is shown below in FIG. 9. Although the shape is similar, the curve recorded using the third embodiment is substantially narrower reflecting the higher currents available from the photodiodes.

Shutter detectors for both the second and third embodiments used the ITT F9810J "Gen III" image intensifier and a standard 6199 PMT to sense the light output from its screen.

Figure 10:
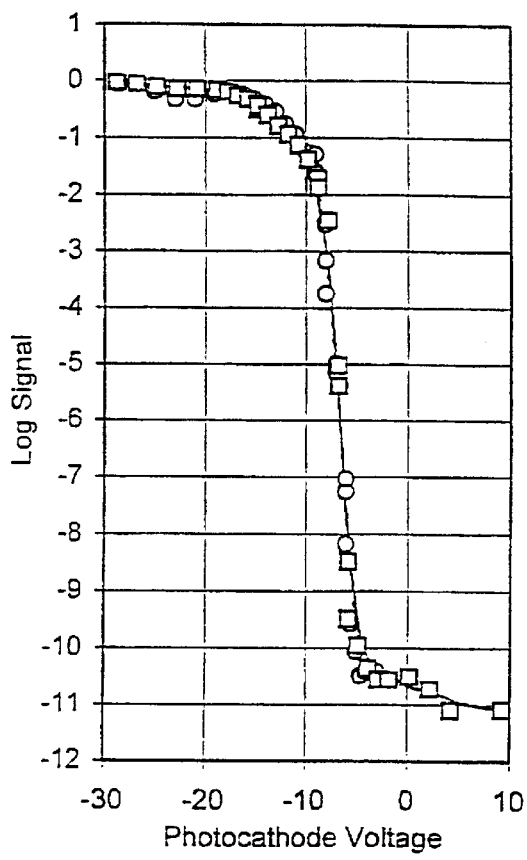
FIG. 10 is a graph showing typical gate biased characteristics of the apparatus constructed in accordance with the third embodiment of the present invention.

Besides shutter speed, an equally important parameter is shutter ratio. As described above, this is the ratio of the "off" sensitivity to the "on" sensitivity. It is also referred to as the "switching ratio." The shutter ratio of the third embodiment was measured by recording the signal out of the shutter detector as a function of bias voltage using synchronized light pulses from the laser as input and a calibrated set of neutral density filters. The result for two wavelengths (510 and 830 nm) is shown in FIG. 10. The 510 nm data are the circles to which a dotted curve has been fitted, and the 830 nm data are the boxes to which a solid curve has been fitted. On the scale of this figure, it is hard to separate the two fitted curves. The shutter ratio at either wavelength is about $10^{-11}$.

The third embodiment is operated at a bias of about +65v and a gate pulse of about −85v.

There is more than enough gain to see single photoelectrons and, at these short gate times, thermal emission of electrons from the photocathode (dark current) is negligible. While unfiltered room light might contribute $10^{13}$ photons/$mm^2$/second, this is only $10^4$ photons in a nanosecond, which can be reduced to arbitrarily low levels by using filters, such as fluorescence filter 34, that block all but the laser wavelengths.

Figure 11:
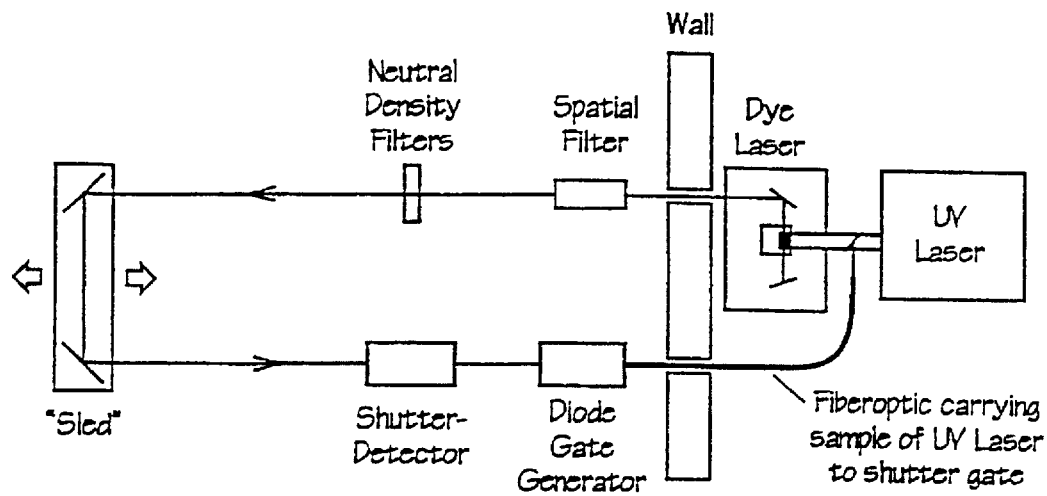
FIG. 11 is a block diagram illustrating a laboratory setup for generating gate delays by changing optical path length in air with a sliding mirror.

Most of the experiments conducted using the present invention depend on taking measurements at various "gate delays." The gate delay is the lag in turning on the shutter relative to the arrival of the light at its input. Zero delay is when the light pulse is centered on the shutter opening. Two ways to generate the delays were used. One depended on the velocity of light in air. The experimental setup is shown in FIG. 11. The UV laser and dye laser are located in a laboratory area while the shutter detector and optical parts are located in a darkroom. The sled is mounted on rails and optical delays are achieved by sliding it to increase or decrease the path length. The reflector was variously a pair of right-angle prisms, a corner cube, or simply a flat aluminized mirror. The gate generator is triggered by a small fraction (the reflection off of a piece of glass) of the light from the UV laser carried by three optical fibers to the three photodiodes.

Figure 12:
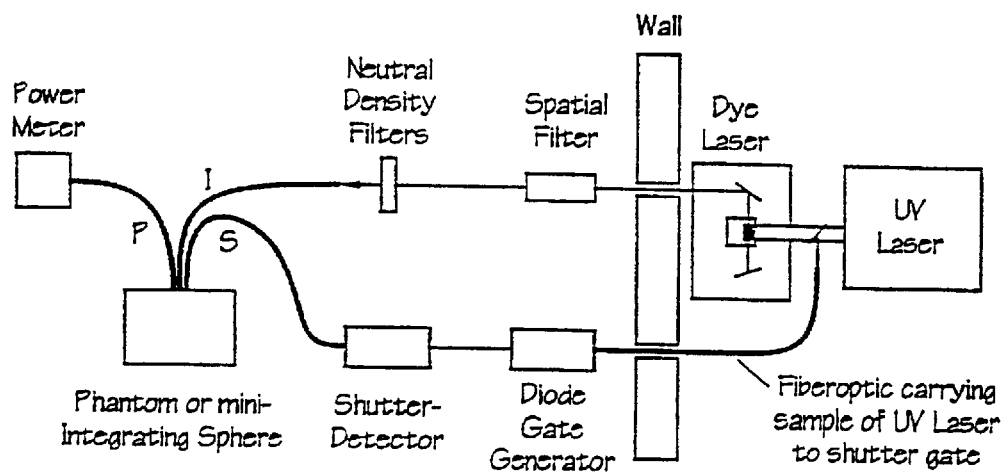
FIG. 12 is a block diagram illustrating an alternative method for generating gate delay using fiberoptic cables.

The other method of generating delays is shown in FIG. 12. Here delays are achieved by changing the length of the optical fiber that carries the light from the laser to the phantom (or integrating sphere). Comparisons between the two systems show the velocity in the fiber to be 18.6 cm per nanosecond. All cable used was 2 mm plastic fiber jacketed to an overall diameter of 3 mm. Specifically, Mitsubishi ESKA Optical Grade polymethyl-methacrylate, Edmund Scientific #A2551 was used.

Figure 13:
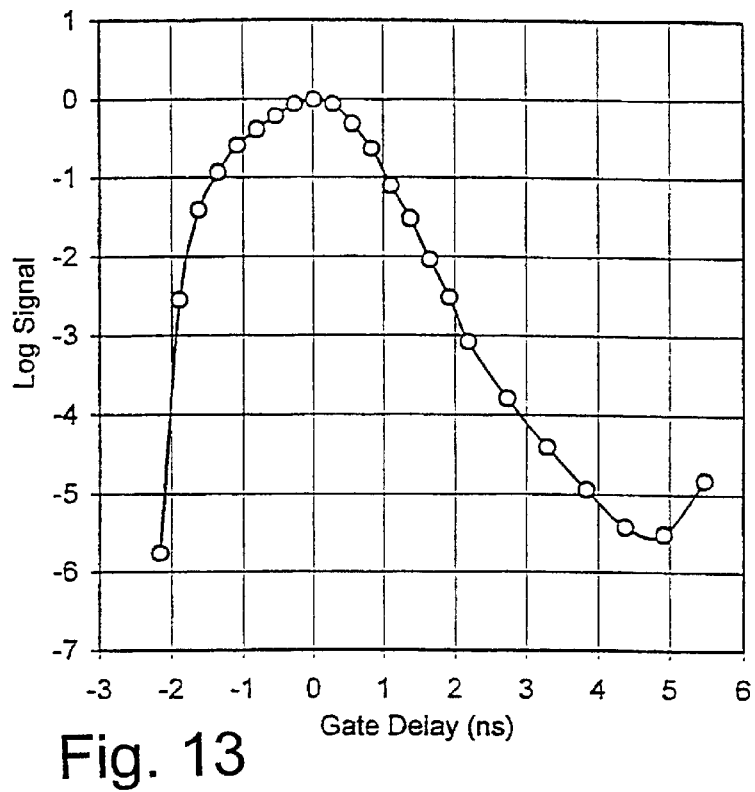
FIG. 13 is a graph showing a typical gate delay curve subject to delayed gate persistence.

FIG. 13 shows the typical result of a gate delay study. In this case, the fiberoptic method was used with the integrating sphere. The length of the injection cable "I" was stepped in units of 51 mm (about 273 ps). Input power was monitored by a connection from the integrating sphere to the power meter. A fixed-length cable (4.36 ns) connected the shutter detector to the integrating sphere.

Although there is a very abrupt drop in signal for light arriving before the shutter turns on, there remains a very small "persistent" signal when the shutter is turned on well after the light pulse is supposed to be over. This phenomenon is referred to herein as "delayed gate persistence." A number of causes were investigated and are discussed below.

The most obvious is that the UV laser, or dye laser by itself, is not fully extinguishing and a very small emission of light remains. This has been tested with spatial filtering and very narrow-band interference filters without a clear-cut conclusion. Some late light may be coming from light held up in the integrating sphere. Another explanation is fluorescence of the glass windows of the image intensifier. This is very likely a part of the explanation at the shorter wavelengths, since there is always more delayed persistence at 510 nm than the infrared. Late light from reverberations in the optical paths are avoidable by making the cables long enough so that any echo arrives after the measurement is over. The beginnings of a first echo are shown in the last point in FIG. 13. Any fluorescence in the cables will be shifted to lower wavelengths and can be filtered out at the shutter input using fluorescence filter 34.

Persistence may also be due to how the image intensifier deals with the emission of huge numbers of photoelectrons when the photocathode space is reversed bias. Perhaps some are left with enough energy to be drawn into the MCP when the shutter is turned on. Others have observed similar effects that were dependent on the make of the intensifier (Yates et al., 1984).

At the present level of this persistence, simulations show that it is not a problem for optode separations of several millimeters. Should it become a problem that will not go away with improved laser and image intensifier design, it can always be dealt with by adding auxiliary optical shutters 14 and/or 32, such as Kerr and Pockels cells. Although they have limited shutter ratios, they could be used to reduce any after-light from the laser by two decades or, if placed in front of one or both the shuttered detectors, block the injection light by the same amount.

A phantom experiment was conducted to serve two purposes. The first is to demonstrate conclusively that IRPS technology is sensitive to depths of several centimeters with injecting and receiving optodes only a few millimeters apart. The second is to provide a wide range of accurate experimental data for validating the computer models. These models can then be used to predict with confidence the performance of related configurations.

Figure 14:
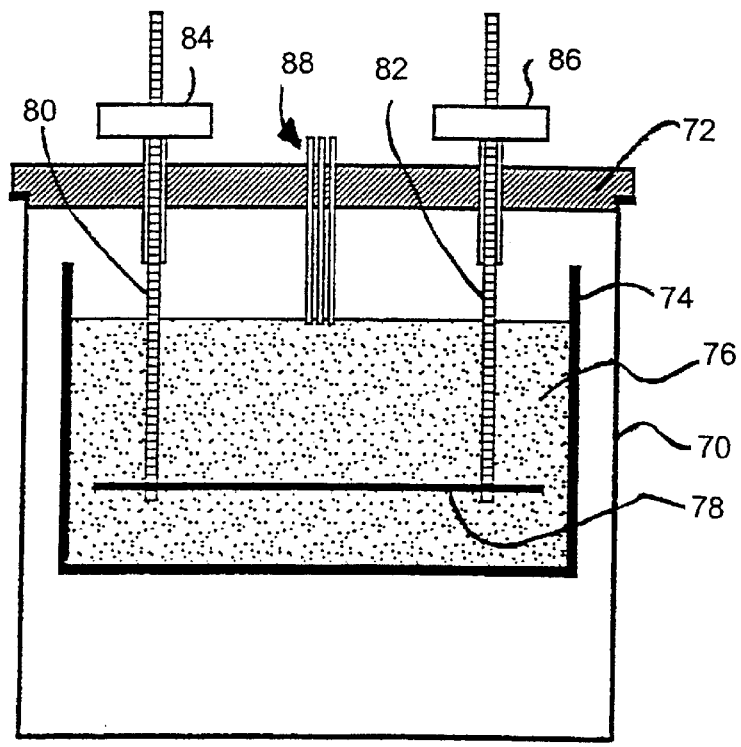
FIG. 14 is a cross-sectional view of a phantom experiment setup used to test the apparatus constructed in accordance with the present invention.

Basically, the phantom setup consists of a tank of scattering material with means for holding fiberoptic cables close together at its surface. A planar absorber is held parallel to the surface with means for adjusting its distance from the surface. A sketch of the phantom is shown in FIG. 14. The outside is a 25 cm diameter by 25 cm deep stainless steel "stock pot" 70 with a thick, close-fitting wooden lid 72. It is lined on the sides with special black paper and the bottom is painted flat black using Krylon® 1602 Ultra Flat Black, Solon, Ohio 44139, as are all surfaces of lid 72. A second thick-walled aluminum container 74, 17 cm in diameter and 13 cm deep and painted flat black on all surfaces, holds a scattering solution 76. An absorber 78 is provided that is a flat, 15 cm diameter plastic disk also painted flat black on all surfaces. Absorber 78 is suspended from lid 72 on two, 10–24 threaded rods 80 and 82. The plate can be raised or lowered by turning threaded knobs 84 and 86 (one turn equals 1.06 mm). Penetrating the center of lid 72 are three, closely-spaced, thin-walled aluminum tubes 88 into which the fiberoptic cables are inserted. Their inside diameter provides a smooth fit for the jacketed cables, and a slight constriction at the end provides a stop for reproducible positioning of the cables. The tubes were 5 mm center-to-center, which is less than the diameter of the heart rate monitor hook electrode shown in FIG. 2.

The scattering medium 76 is 100 g/L of Cremora® non-dairy coffee cream in distilled water. This is a material and concentration for simulating spatial distributions of photons in the adult human head. It makes a very stable suspension that lasts for many days. A yeast solution with a concentration of 10g/L was tried as suggested for the neonatal head (Benaron and Stevenson, 1994). However, it was much too thin and likely to considerably overestimate our depth sensing ability.

The first experiment was to acquire a "gate delay" curve by varying the length of the injector cable while holding the shutter cable fixed at 4.36 ns. Calibrated neutral density filters were used to cover the large dynamic range of the data. The wavelength was 830 nm and the absorber was out of the way at 50 mm from the surface. The resulting data are shown as circles in FIG. 15. The solid line is the theoretical result of a time-dependent diffusion model. The only adjustable parameters involved in optimizing the fit to the data are the absorption and reduced scattering coefficients of the Cremora® solution, which turned out to be $\mu_a$=0.024 cm$^{-1}$ and $\mu_s'$=27 cm$^{-1}$.

Figure 16:
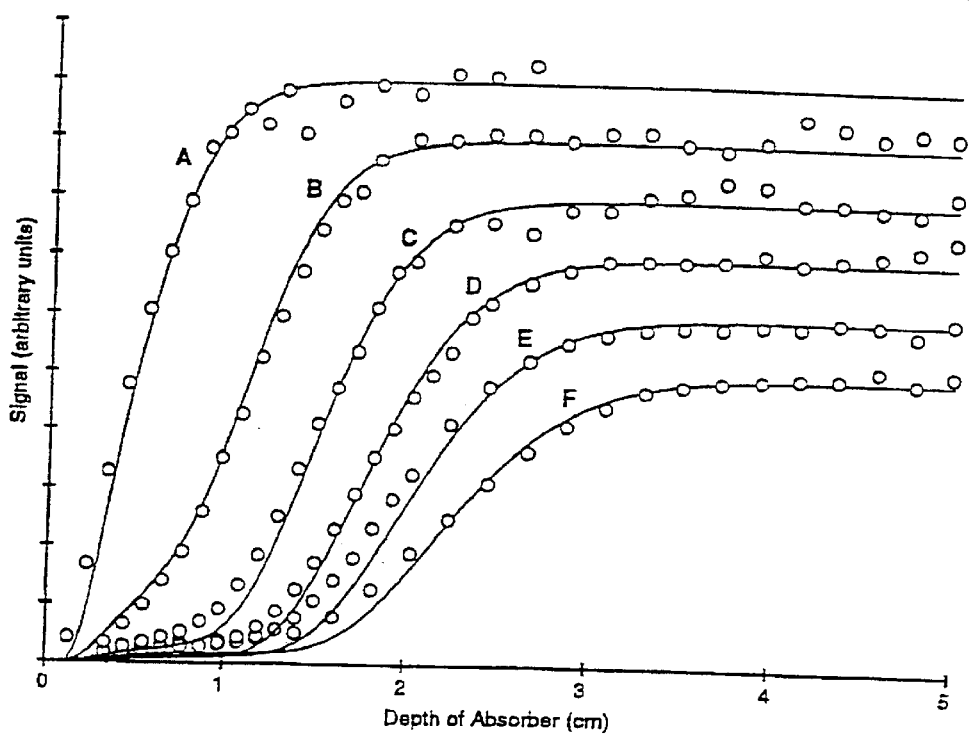
FIG. 16 is a graph showing signals as a function of an absorber depth for various gate delays.

Then several gate delays were selected ("A, B," etc.), and a family of curves were taken as a function of depth of the absorber at these fixed delays. The resulting data are shown as circles in FIG. 16. Again, using the time-dependent diffusion model, the solid lines are the theoretical curves using the previously-determined Cremora® parameters. Initially, raising the absorber has no effect on the observed signal for any of the six gate delay times. At a depth of about 3.5 cm, curve "F," corresponding to the longest delay (7.5 ns), starts to fall. This defines the maximum penetration depth of photons, which take 7.5 ns to return. As the absorber is moved closer to the surface, the other signals, corresponding to shorter delays, respond in the proper sequence. A square-root dependence of diffusion radius on time, $r_D=\sqrt{(2Dt)}$ where D is the diffusion constant, is seen in the location of the break points as a function of delay where $r_D$ corresponds to depth and t to delay.

Figure 15:
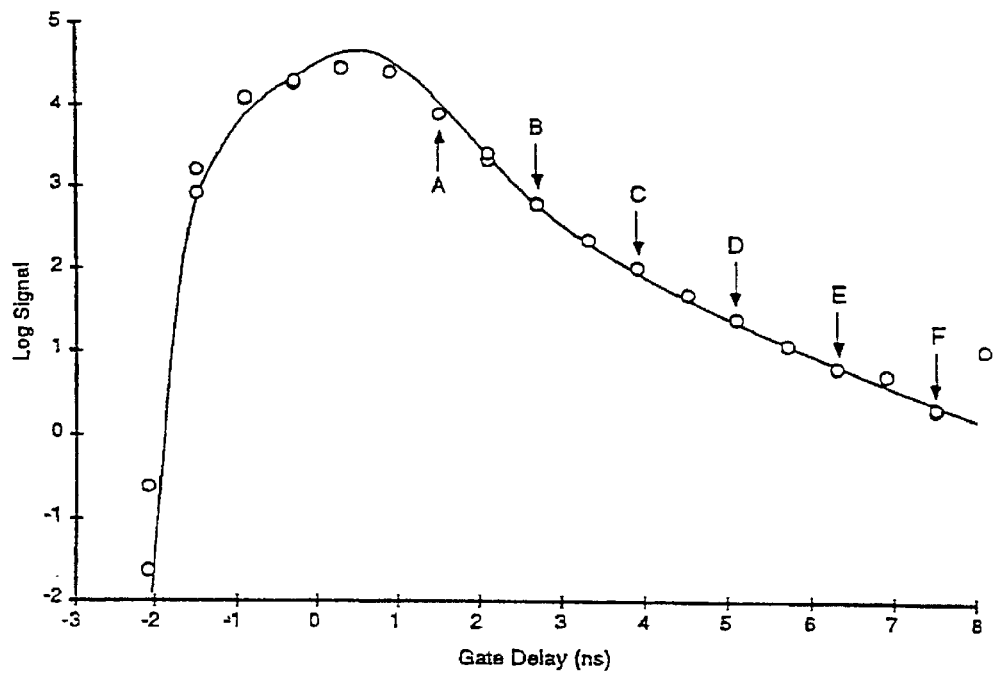
FIG. 15 is a graph illustrating the gate delay curve with the absorber shown in FIG. 14 positioned at five centimeters from the surface of the absorbing material.

In the process of matching the simulations to the data, it was observed that varying $\mu_a$ had no effect on the location of the break points but had a large impact on the fit to FIG. 15. As was deduced from the random walk model, for a given delay absorption determines the number of returning photons while scattering determines their penetration depth.

Photons may thus be seen that have scattered into the medium up to a depth of at least 2.5 cm depending on the gate delay. This is convincing proof that tissue may be sampled at useful depths with optodes placed close together.

Figure 17:
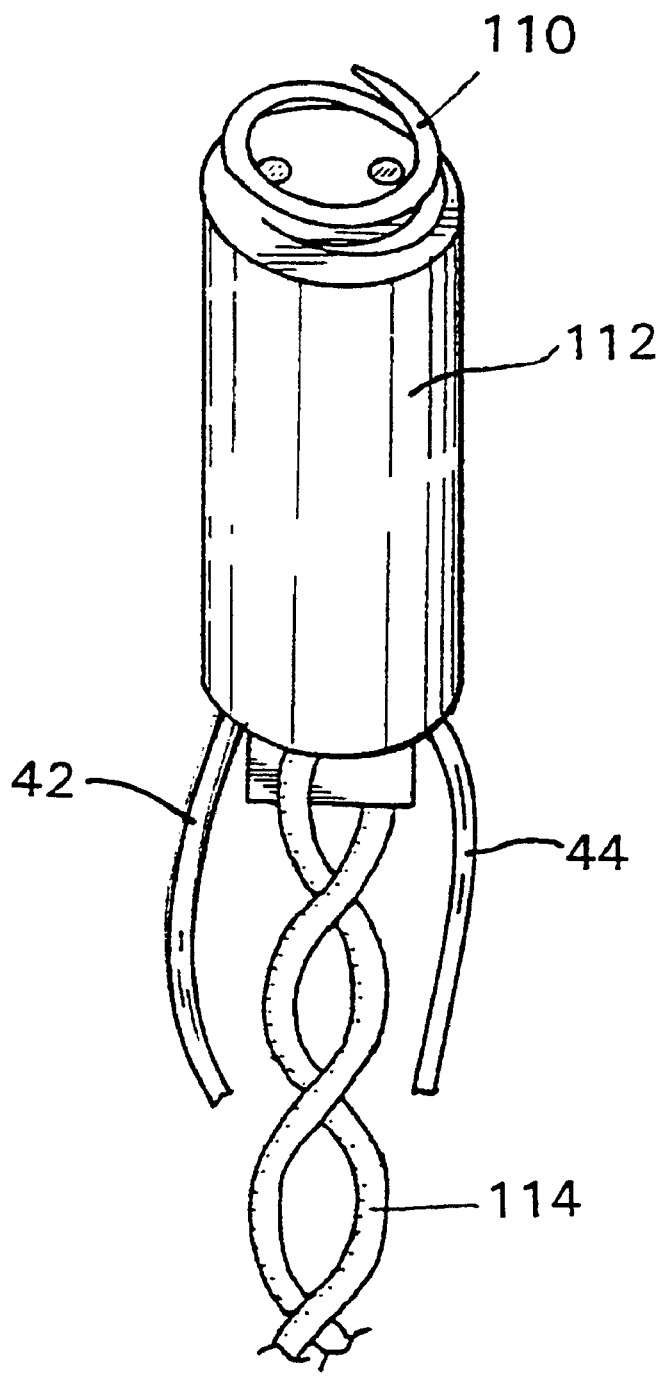
FIG. 17 is a photograph of a hook electrode of the type that may be used with the present invention.

One possibility for connecting the optodes to the head of the fetus is "piggy-backing" of optodes on the widely-used electrode or probe 50 that is hooked into the fetal scalp to monitor a fetal heart rate as described above. A probe 50 in the form of a typical hook electrode 100 available from Life Trace Fetal Monitoring Spiral Electrode, Graphic Controls, Medical Products Division, is shown in FIG. 17. This device comprises a small, stainless steel helical hook 110 connected to a plastic cylinder 112 about 6 mm in diameter and 11 mm long. In using this type of probe to carry out the present invention, in addition to the twisted wire 114 carrying the electrical signal, flexible optical fibers 42 and 44 disposed along side the twisted wire 114 would both inject light into the head and collect light from the head using the same contact.

The optode spacing in the phantom studies was 5 mm. Optode spacings of 3–4 mm will be sufficient at our present delayed gate persistence levels. It is expected that persistence levels can be reduced sufficiently to permit spacings of 2–3 mm. All of these separations are well within the size of the present "hook" probes used for heart rate monitoring. Thixotropic gels containing an absorber to absorb cross-talk might improve the optical properties of the interface if they can be conveniently applied, remain stable, and are biologically inert. By providing a thin film of such an absorbing gel, noise introduced at the probe/scalp interface may be significantly reduced. Because such a gel would be applied in a thin film, the gel would not absorb any significant level of injected or received photons since the photons travel through the film at its thinnest dimension. Any noise in the form of light, however, must traverse the thin film in a perpendicular direction to the injected photons, and thus, must travel through the thickest dimension of the film. Because such a light absorbing gel is much more absorbent across its thickest dimension, substantially all of the noise is absorbed by the gel.

The above description is considered that of the preferred embodiments only. Modifications of the invention will occur to those skilled in the art and to those who make or use the invention. Therefore, it is understood that the embodiments shown in the drawings and described above are merely for illustrative purposes and not intended to limit the scope of the invention, which is defined by the following claims as interpreted according to the principles of patent law, including the Doctrine of Equivalents.

The invention claimed is:

1. An apparatus for monitoring fetal cerebral oxygenation during childbirth comprising:
   a source of infrared photons;
   a probe to optically access a single location on the scalp of a fetus by injecting the infrared photons generated by said photon source at said location, and for receiving scattered photons reflected from within the skull of the fetus at said location; and
   at least first and second detectors for detecting the presence of photons received by said probe at at least two different delay intervals so as to provide for distinguishing photons reflected at different instants or from different depths within the head of the fetus on the basis of said different delay intervals.

2. The apparatus as defined in claim 1, wherein said probe includes a photon injection site and a photon reception site that are within about 5 mm or less of each other.

3. The apparatus as defined in claim 1, wherein said photon source is a laser.

4. The apparatus as defined in claim 1, wherein said photon source emits a pulse of photons that are subsequently injected into the head of the fetus.

5. The apparatus as defined in claim 4, wherein the pulse of photons emitted from said photon source is less than about 1 ns in duration.

6. The apparatus as defined in claim 1, wherein said photon source emits near-infrared photons.

7. The apparatus as defined in claim 1, and further including a first fiberoptic cable optically coupling said photon source to said probe, and a second fiberoptic cable optically coupling said probe to said first and second detector.

8. The apparatus as defined in claim 1, wherein said first and second detectors are shuttered detectors, said first and second shuttered detectors each having a trigger input and detecting photons only during an interval when a trigger signal is applied to its trigger input.

9. The apparatus as defined in claim 8, wherein said photon source emits a pulse of photons that are subsequently injected into the head of the fetus, and wherein said apparatus further includes a beam splitter positioned between said photon source and said probe for transmitting a pulse of photons as a trigger signal to the trigger inputs of said first and second shuttered detectors at the same time the pulse of photons is transmitted to said probe.

10. The apparatus as defined in claim 9, and further including a first fiberoptic cable for transmitting the pulse of photons from said beam splitter to the trigger input of said first shuttered detector, and a second fiberoptic cable for transmitting the pulse of photons from said beam splitter to the trigger input of said second shuttered detector, said first and second fiberoptic cables having different lengths so as to trigger said first and second shuttered detectors at different delay times.

11. The apparatus as defined in claim 8, wherein said first and second shuttered detectors are configured to gate on and off in about 1 ns or less.

12. The apparatus as defined in claim 8, wherein said first and second shuttered detectors include image intensifiers.

13. The apparatus as defined in claim 12, wherein photons received from said probe are focussed onto a peripheral region of a photocathode of said image intensifiers.

14. The apparatus as defined in claim 1, and further including a fluorescence filter positioned between said probe and at least one of said first and second detectors.

15. The apparatus as defined in claim 1, and further including a photodetector and a beam splitter positioned between said probe and said first and second detectors so as to transmit a portion of the photons received from said probe to said photodetector.

16. The apparatus as defined in claim 1, wherein said photon source generates sequential pulses of photons at at least two different wavelengths.

17. A method for monitoring cerebral oxygenation of a human subject comprising the steps of:
   generating a pulse of near-infrared photons;
   injecting at least a portion of the generated pulse of photons into the scalp of the subject;
   receiving scattered photons reflected from within the skull of the subject; and
   detecting the presence of received photons at at least two different delay intervals relative to the generation of the pulse of photons so as to provide for distinguishing photons reflected at different instances or from different depths from within the head of the subject.

18. The method as defined in claim 17, and further including the step of determining relative quantity of photons at said two different delay intervals.

19. The method as defined in claim 18, and further including the step of using relative values to determine absorption and/or said different depths.

20. An apparatus for spectrophotometric analysis of an object, said apparatus comprising:
   a source for emitting a pulse of photons that is injected into the object;
   a photon receiver for receiving photons reflected from within the object;
   a first shuttered detector having a trigger input for detecting the presence of photons received through said photon receiver during a first interval determined by a gating pulse applied to said trigger input;
   a second shuttered detector having a trigger input for detecting the presence of photons received through said photon receiver during a second interval determined by a gating pulse applied to said trigger input;
   a beam splitter in operative alignment with said photon source for splitting the pulse of photons emitted from said photon source;
   a first fiberoptic cable coupled to the trigger input of said first shuttered detector and positioned relative to said beam splitter so as to receive the split photon pulse and deliver a gating pulse to the trigger input of said first shuttered detector; and
   a second fiberoptic cable coupled to the trigger input of said second shuttered detector and positioned relative to said beam splitter so as to receive the split photon pulse and deliver a gating pulse to the trigger input of said second shuttered detector.

21. The apparatus as defined in claim 20, wherein said second fiberoptic cable is longer than said first fiberoptic cable so as to further delay the second interval during which said second shuttered detector receives photons from said photon receiver.

22. The apparatus as defined in claim 20, wherein said first and second shuttered detectors are configured to gate on and off in about 1 ns or less.

23. The apparatus as defined in claim 20, wherein said first and second shuttered detectors include image intensifiers.

24. The apparatus as defined in claim 23, wherein photons received from said photon receiver are focussed onto a peripheral region of a photocathode of each of said image intensifiers.

25. The apparatus as defined in claim 20, and further including a fluorescence filter positioned between said photon receiver and at least one of said first and second shuttered detectors.

26. The apparatus as defined in claim 20, and further including a photodetector and a second beam splitter positioned between said photon receiver and said first and second shuttered detectors so as to transmit a portion of the photons received from said photon receiver to said photodetector.

27. The apparatus as defined in claim 20, wherein said photon source is a laser.

28. The apparatus as defined in claim 20, wherein the pulse of photons emitted from said photon source is less than about 1 ns in duration.

29. The apparatus as defined in claim 20, wherein said photon source emits near-infrared photons.

30. The apparatus as defined in claim 20, and further including a third fiberoptic cable optically coupling said photon receiver to said first and second shuttered detectors.

* * * * *